(12) United States Patent
Krivoruchko et al.

(10) Patent No.: US 7,955,383 B2
(45) Date of Patent: Jun. 7, 2011

(54) LAMINATED IMPLANTABLE MEDICAL DEVICE HAVING A METALLIC COATING

(75) Inventors: Michael Krivoruchko, Forestville, CA (US); Matthew Birdsall, Santa Rosa, CA (US)

(73) Assignee: Medtronics Vascular, Inc., Santa Rosa, CA (US)

(*) Notice: Subject to any disclaimer, the term of this patent is extended or adjusted under 35 U.S.C. 154(b) by 737 days.

(21) Appl. No.: 11/380,134

(22) Filed: Apr. 25, 2006

(65) Prior Publication Data

US 2007/0250158 A1 Oct. 25, 2007

(51) Int. Cl.
*A61F 2/06* (2006.01)
(52) U.S. Cl. ..................... 623/1.44; 623/1.46
(58) Field of Classification Search ........ 623/1.42–1.46; 427/2.24, 2.25
See application file for complete search history.

(56) References Cited

U.S. PATENT DOCUMENTS

| | | | |
|---|---|---|---|
| 3,795,047 A * | 3/1974 | Abolafia et al. ............... 29/843 |
| 4,733,665 A | 3/1988 | Palmaz | |
| 4,739,762 A | 4/1988 | Palmaz | |
| 4,800,882 A | 1/1989 | Gianturco | |
| 4,886,062 A | 12/1989 | Wiktor | |
| 5,133,732 A | 7/1992 | Wiktor | |
| 5,292,331 A | 3/1994 | Boneau | |
| 5,314,472 A | 5/1994 | Fontaine | |
| 5,421,955 A | 6/1995 | Lau et al. | |
| 5,679,470 A | 10/1997 | Mayer | |
| 5,817,152 A | 10/1998 | Birdsall et al. | |
| 5,913,897 A | 6/1999 | Corso et al. | |
| 5,935,162 A | 8/1999 | Dang | |
| 6,019,784 A | 2/2000 | Hines | |
| 6,027,528 A | 2/2000 | Tomonto et al. | |
| 6,090,127 A | 7/2000 | Globerman | |
| 6,114,049 A | 9/2000 | Richter | |
| 6,174,329 B1 * | 1/2001 | Callol et al. ............... 623/1.34 |
| 6,379,383 B1 | 4/2002 | Palmaz et al. | |
| 6,387,121 B1 | 5/2002 | Alt | |
| 6,419,693 B1 | 7/2002 | Fariabi | |
| 6,508,832 B1 * | 1/2003 | Jalisi et al. ............... 623/1.15 |
| 6,638,301 B1 * | 10/2003 | Chandrasekaran et al. . 623/1.34 |
| 6,730,116 B1 | 5/2004 | Wolinsky et al. | |
| 6,865,810 B2 | 3/2005 | Stinson | |
| 6,866,805 B2 | 3/2005 | Hong et al. | |
| 2002/0004060 A1 | 1/2002 | Heublein et al. | |
| 2002/0013616 A1 | 1/2002 | Carter et al. | |
| 2003/0059640 A1 | 3/2003 | Marton et al. | |
| 2004/0158314 A1 | 8/2004 | Hogendijk | |
| 2004/0186556 A1 | 9/2004 | Hogendijk et al. | |
| 2004/0243225 A1 * | 12/2004 | Ragheb et al. ............... 623/1.42 |
| 2005/0060020 A1 | 3/2005 | Jenson | |
| 2005/0071016 A1 | 3/2005 | Hausdorf et al. | |
| 2005/0090888 A1 | 4/2005 | Hines et al. | |
| 2005/0098241 A1 | 5/2005 | Wachter et al. | |

(Continued)

FOREIGN PATENT DOCUMENTS

WO WO98/31304 7/1998

(Continued)

*Primary Examiner* — David Isabella
*Assistant Examiner* — Yashita Sharma

(57) ABSTRACT

A laminated stent encapsulated with a metal coating is provided. The metal coating may be a very thin metal coating. Portions of the metal coating may be removed such that the metal coating covers voids in the laminate, particularly in the area where the different layers of the laminated stent come together. The metal coating for the laminated stent may be provided by sputtering, such as vacuum deposition or ion beam sputtering, spraying, dipping, or other known methods.

6 Claims, 4 Drawing Sheets

U.S. PATENT DOCUMENTS

2006/0015173 A1   1/2006   Clifford et al.

FOREIGN PATENT DOCUMENTS

| | | |
|---|---|---|
| WO | WO 00/32273 | 6/2000 |
| WO | WO00/50100 | 8/2000 |
| WO | WO00/54704 | 9/2000 |
| WO | WO01/41829 | 6/2001 |
| WO | WO 03/094735 | 11/2003 |
| WO | WO 2004/108346 | 12/2004 |
| WO | WO 2005/013856 | 2/2005 |
| WO | WO 2005/025453 | 3/2005 |
| WO | WO 2005/026399 | 3/2005 |
| WO | WO 2005/044361 | 5/2005 |

* cited by examiner

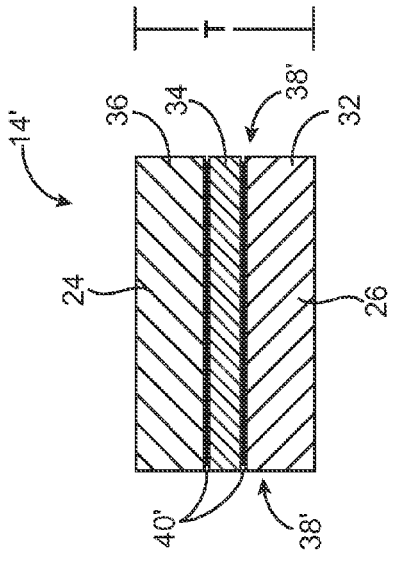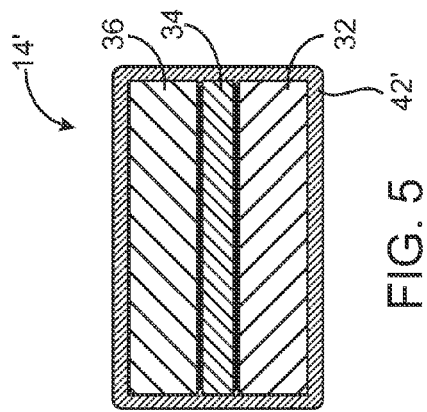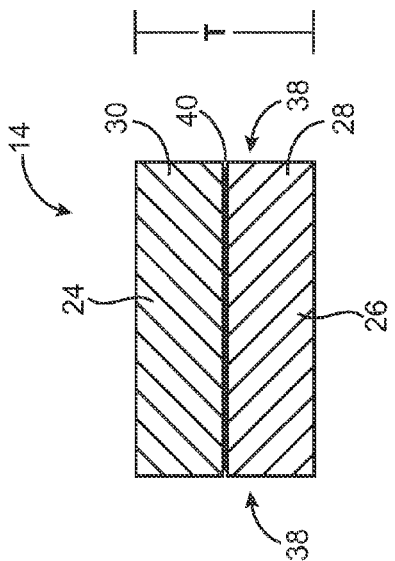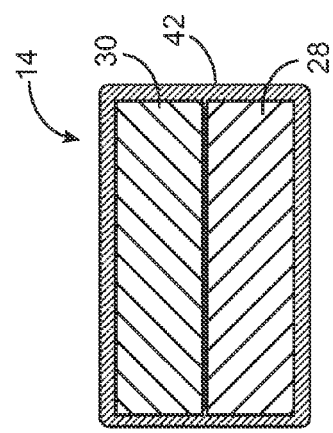

LAMINATED IMPLANTABLE MEDICAL DEVICE HAVING A METALLIC COATING

FIELD OF THE INVENTION

This invention relates generally to coatings for laminated implantable medical devices. More particularly, the present invention is directed to metal coatings for laminated metal stents and grafts.

BACKGROUND OF THE INVENTION

Stents are generally cylindrically shaped devices that are radially expandable to hold open a segment of a blood vessel or other anatomical lumen after implantation into the body lumen. Stents have been developed with coatings to deliver drugs or other therapeutic agents.

Various types of stents are in use, including balloon expandable and self-expanding stents. Balloon expandable stents generally are conveyed to the area to be treated on balloon catheters or other expandable devices. For insertion, the stent is positioned in a compressed configuration along the delivery device, for example crimped onto a balloon that is folded or otherwise wrapped about a guide catheter that is part of the delivery device. After the stent is positioned across the lesion, it is expanded by the delivery device, causing the stent diameter to expand. For a self-expanding stent, commonly a sheath is retracted, allowing expansion of the stent.

Stents are used in conjunction with balloon catheters in a variety of medical therapeutic applications including intravascular angioplasty. For example, a balloon catheter device is inflated during PTCA (percutaneous transluminal coronary angioplasty) to dilate a stenotic blood vessel. The stenosis may be the result of a lesion such as a plaque or thrombus. After inflation, the pressurized balloon exerts a compressive force on the lesion thereby increasing the inner diameter of the affected vessel. The increased interior vessel diameter facilitates improved blood flow. Soon after the procedure, however, a significant proportion of treated vessels re-narrow or collapse.

To prevent acute vessel narrowing or collapse, short flexible cylinders, or stents, constructed of metal or various polymers are implanted within the vessel to maintain lumen size. The stent acts as a scaffold to support the lumen in an open position. Various configurations of stents include a cylindrical tube defined by a mesh, interconnected stents or like segments. Some exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz and U.S. Pat. No. 5,421,955 to Lau. Balloon-expandable stents are mounted on a collapsed balloon at a diameter smaller than when the stents are deployed. Stents can also be self-expanding, growing to a final diameter when deployed without mechanical assistance from a balloon or like device.

Stents have been made of various materials, including various metals and polymers. Various metals and alloys, such as stainless steel and MP35N have been successfully used as stent materials. However, no material is a perfect stent material. Each has its particular advantages and disadvantages. Therefore, some recent stents have attempted to combine the advantageous properties of different materials by laminating layers of different material to form the struts of a stent. Such stents are known as "laminated stents". For example, Abbot Laboratories is marketing a product known as the TriMaxx® stent that is a laminated metal stent. In particular, the TriMaxx® stent includes a layer of tantalum sandwiched between two layers of stainless steel.

The circumferential surface of a strut of a laminated metal stent design includes different materials. These different materials can pose difficulties in coating such a laminated stent with, for example, a drug eluting polymer. Further, these different materials may provide a driving force for galvanic corrosion of the stent and present non-homogeneous mechanical properties, such as flexibility characteristics. Still further, the different layers of a laminated stent may come apart or de-laminate over time on some portions of the stent.

BRIEF SUMMARY OF THE INVENTION

A laminated stent encapsulated with a metal coating is provided. The metal coating may be a very thin metal coating. Portions of the metal coating may be removed such that the metal coating covers at least voids in the laminate, particularly in the area where the different metals of the laminated stent come together. The metal coating for the laminated stent may be provided by sputtering, such as vacuum deposition or ion beam sputtering, chemical vapor deposition (CVD), spraying, dipping, or other methods known to those skilled in the art.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 2 illustrates a cross-sectional view of a stent strut of the stent of FIG. 1 taken along line A-A, showing a two layer laminated construction prior to coating.

FIG. 3 illustrates a cross-sectional view of an alternative stent strut of the stent of FIG. 1 taken along line A-A, showing a three layer laminated construction prior to coating.

FIG. 4 illustrates a cross-sectional view of a stent strut of FIG. 2 in accordance with an embodiment of the present invention.

FIG. 5 illustrates a cross-sectional view of the strut of FIG. 3 in accordance with an embodiment of the present invention.

DETAILED DESCRIPTION OF THE INVENTION

Specific embodiments of the present invention are now described with reference to the figures, where like reference numbers indicate identical or functionally similar elements.

Figure 1:
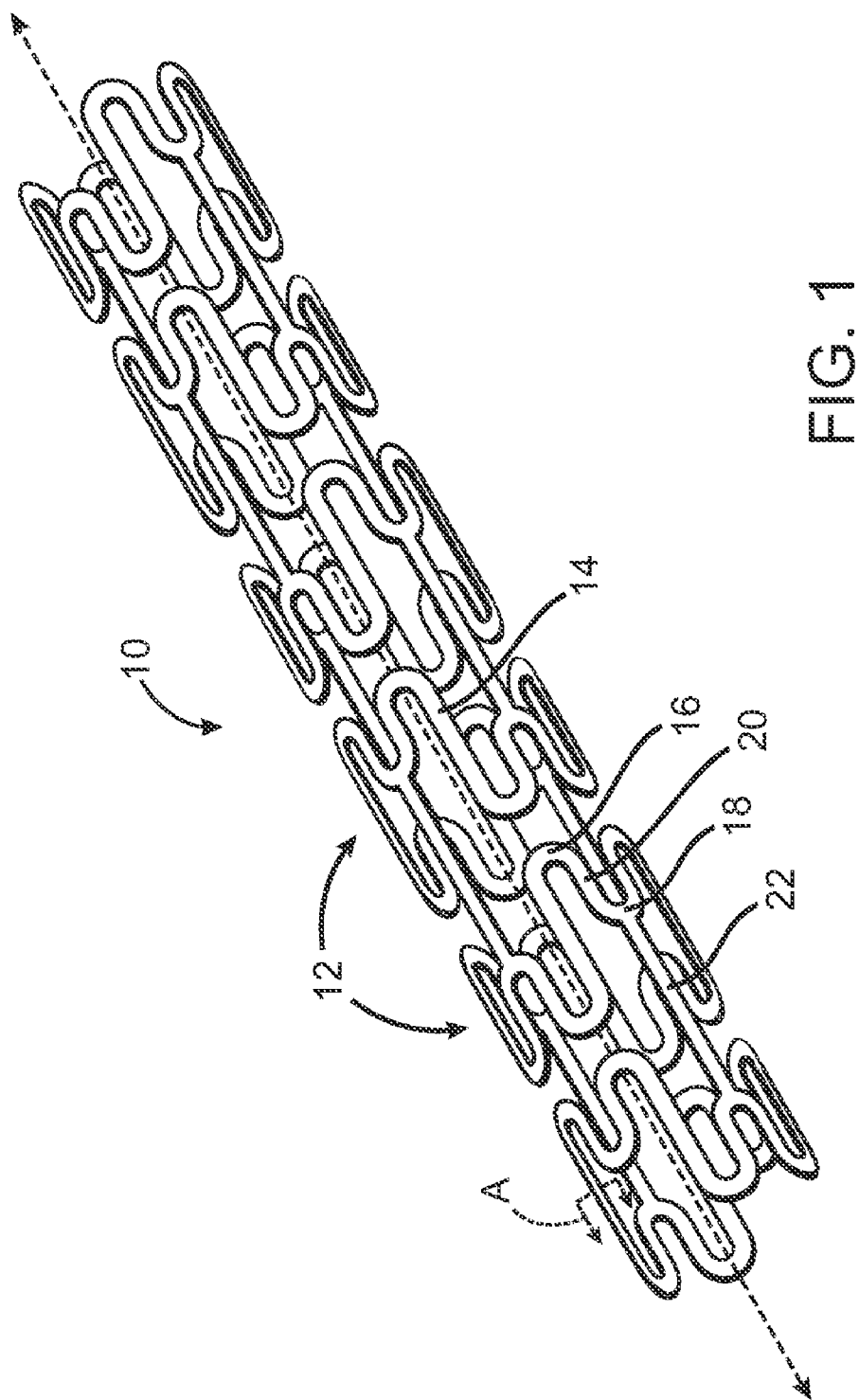
FIG. 1 is a perspective view of an exemplary stent of in accordance with an embodiment of the present invention.

The present invention provides a laminated stent or graft, which are often referred to as endoprostheses, with a metal coating. FIG. 1 illustrates an exemplary stent 10 in accordance with an embodiment of the present invention. Stent 10 is a patterned tubular device that includes a plurality of radially expandable cylindrical rings 12. Cylindrical rings 12 are formed from struts 14 formed in a generally sinusoidal pattern including peaks 16, valleys 18, and generally straight segments 20 connecting peaks 16 and valleys 18. Connecting links 22 connect adjacent cylindrical rings 12 together. In FIG. 1, connecting links 22 are shown as generally straight links connecting a peak 16 of one ring 12 to a valley 18 of an adjacent ring 12. However, connecting links 22 may connect a peak 16 of one ring 12 to a peak 16 of an adjacent ring, or a valley 18 to a valley 18, or a straight segment 20 to a straight segment 20. Further, connecting links 22 may be curved. Connecting links 22 may also be excluded, with a peak 16 of one ring 12 being directly attached to a valley 18 of an adjacent ring 12, such as by welding, soldering, or the manner in which stent 10 is formed, such as by etching the pattern from a flat sheet or a tube. It will be appreciated by one of ordinary skill in the art that stent 10 of FIG. 1 is merely an exemplary stent and that stents of various forms and methods of fabrication can be used. For example, in a typical method of making a stent, a thin-walled, small diameter metallic tube is cut to produce the desired stent pattern, using methods such as laser cutting or chemical etching. The cut stent may then be descaled, polished, cleaned and rinsed. Some examples of methods of forming stents and structures for stents are shown in U.S. Pat. No. 4,733,665 to Palmaz, U.S. Pat. No. 4,800,882 to Gianturco, U.S. Pat. No. 4,886,062 to Wiktor, U.S. Pat. No. 5,133,732 to Wiktor, U.S. Pat. No. 5,292,331 to Boneau, U.S. Pat. No. 5,421,955 to Lau, U.S. Pat. No. 5,935,162 to Dang, U.S. Pat. No. 6,090,127 to Globerman, and U.S. Pat. No. 6,730,116 to Wolinsky et al., each of which is incorporated by reference herein in its entirety.

FIG. 2 is a cross-sectional view taken at A-A of FIG. 1 through a portion of strut 14 of stent 10 prior to adding a metal coating. Strut 14 has a suitable thickness T between the strut outer surface 24 and an inner surface 26. Typically, thickness T may be in the range of approximately 50 μm (0.002 inches) to 200 μm (0.008 inches). As shown in FIG. 2, strut 14 has a laminated construction made of a first layer 28 and a second layer 30. First layer 28 and second layer 30 may be any material that is typically used for a stent, for example, stainless steel, "MP35N," "MP20N," nickel titanium alloys such as Nitinol, tantalum, platinum-iridium alloy, gold, magnesium, L605, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Preferably, first layer 28 and second layer 30 are different materials. First layer 28 and second layer 30 are bonded using diffusion bonding, friction welding, explosion welding, sintering, hot isostatic pressing (HIP), electroplating, and other bonding techniques as would be known to those of ordinary skill in the art.

FIG. 3 is a cross-sectional view taken at A-A of FIG. 1 and illustrates an alternative embodiment of a strut 14' of stent 10 prior to adding a metal coating. Strut 14' of FIG. 3 is a three-layer laminate, including inner layer 32, middle layer 34, and outer layer 36. Each layer may be made of materials typically used in stents, for example, those listed above with respect to FIG. 2. as well as radiopaque materials not commonly used for stents like iridium, palladium, osmium, tungsten etc., and biodegradable metals like magnesium alloys, zinc and iron alloys, and the like. Each layer 32, 34, and 36 may be made of a different material. Alternatively inner layer 32 and outer layer 36 may be made of the same material and middle layer 34 may be made of a different material.

A cross-sectional view of connecting links 22 of stent may be similar to struts 14, 14' or may be different. For example, a thickness of connecting links 22 may be different than strut 14 of cylindrical rings 12 to provide variable flexibility between the rings 12 and connecting links 22. A specific choice of thickness for struts 14 and links 22 depends on several factors, including, but not limited to, the anatomy and size of the target lumen. Further, struts 14, 14' may be of laminated construction and links 22 may not be a laminated construction.

As seen in FIG. 2, longitudinal voids 40 exist between and along the outer edges of first layer 28 and second layer 30. Further, if first layer 28 and second layer 30 are different materials, side surfaces 38 of strut 14 present two different materials to the surrounding environment. Similarly, strut 14' shown in FIG. 3 includes voids 40' between inner layer 32 and middle layer 34, and between middle layer 34 and outer layer 36. Further, if any of layers 32, 34, and 36 are made of different materials, side surfaces 38' of strut 14 present different materials to the surrounding environment.

FIG. 4 illustrates strut 14 of FIG. 2 with a metal coating 42 surrounding first layer 28 and second layer 30. Metal coating 42 fills in voids 40 and also provides that the entire outer circumference of strut 14 presents a uniform material to the surrounding environment. Metal coating 42 may be made of any metal or combinations of metal, preferably biocompatible metals, as well as bioresorbable metals. For example, metal coating 42 may be selected from, but not limited to, biocompatible, radiopaque metals such as tantalum, iridium, platinum, and molydenum. Alternatively, metal coating 42 may be selected from, but not limited to, biocompatible, biodegradable metals such as zinc, magnesium, and iron. Metal coating 42 may be in the range of 1 μm to 50 μm thick. Metal coating 42 may be provided by sputtering, such as vacuum deposition or ion beam sputtering, chemical vapor deposition (CVD), spraying, dipping, or other methods known to those skilled in the art. FIG. 5 similarly shows strut 14' of FIG. 3 with a metal coating 42' surrounding inner layer 32, middle layer 34, and outer layer 36. Metal coating 42' fills voids 40' between inner layer 32 and middle layer 34, and between middle layer 34 and outer layer 36. Metal coating 42' also provides that the entire outer circumference of strut 14' presents a uniform material to the surrounding environment.

Figure 6:
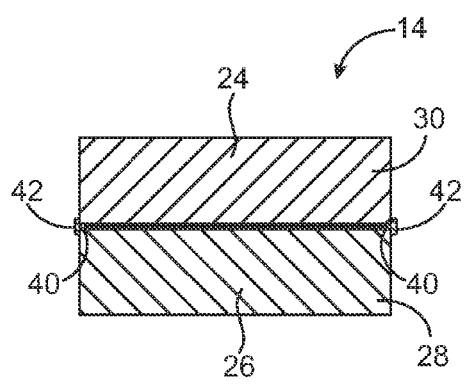
FIG. 6 illustrates a cross-sectional view of the strut of FIG. 4 in accordance with an alternative embodiment of the present invention.
Figure 7:
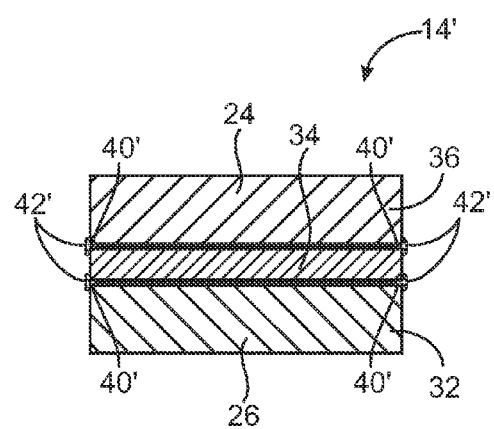
FIG. 7 illustrates a cross-sectional view of the strut of FIG. 5 in accordance with an alternative embodiment of the present invention.

In alternative embodiments of struts 14, 14' as illustrated in FIGS. 6 and 7, after metal coating 42, 42' is applied, metal coating 42, 42' is removed except in the areas of voids 40, 40'. Thus, coating 42, 42' remains only in the area of voids 40, 40'. Metal coating 42, 42' may be removed by electropolishing, ion beam etching, chemical etching, or similar techniques known to those of ordinary skill in the art. Alternatively, metal coating 42, 42' may be applied only to the area of voids 40, 40' such that metal coating 42, 42' fills voids 40, 40' where the layers of the laminated struts meet. Such a metal filling may be applied using techniques such as sputtering and masking using techniques similar to silicon chip fabrication, e.g., coating with photoresist, developing the photoresist, metal coating and resist removal.

The struts 14, 14' of any of the embodiments described above may be coated with one or more therapeutic substances. Methods of coating a stent or other implantable medical device with one or more therapeutic substances, or with a polymer containing one or more therapeutic substances are well-known. For example, one or more therapeutic substances can be added to stent 10 by dissolving or mixing the therapeutic substances in a solvent and applying the therapeutic substance and solvent mixture to stent 10. To cover stent 10 with a polymer containing the therapeutic substance or substance combination, a solution of the polymeric material and one or more therapeutic substances are mixed, often with a solvent, and the polymer mixture is applied to the implantable device. Stent 10 can also be coated with a polymer that does not contain a therapeutic substance, for example, to form a sealant layer over an underlying layer, which does contain a therapeutic substance. Methods of applying the therapeutic substance, polymer, or therapeutic substance and polymer mixture to stent 10 include, but are not limited to, immersion, spray-coating, sputtering, and gas-phase polymerization. Immersion, or dip-coating, entails submerging the entire stent 10, or an entire section of stent 10, in the mixture. Stent 10 is then dried, for instance in a vacuum or oven, to evaporate the solvent, leaving the therapeutic substance or therapeutic substance and polymer coating on the stent. Similarly, spray-coating requires enveloping the entire stent, or an entire section of the stent, in a large cloud of the mixture, and then allowing the solvent to evaporate, to leave the coating. Sputtering typically involves placing a polymeric coating material target in an environment, and applying energy to the target such that polymeric material is emitted from the target. The polymer emitted deposits onto the device, forming a coating. Similarly, gas phase polymerization typically entails applying energy to a monomer in the gas phase within a system set up such that the polymer formed is attracted to a stent, thereby creating a coating around the stent.

The polymer used for coating stent 10 may be either bioabsorbable or biostable. A bioabsorbable polymer bio-degrades or breaks down in the body and is not present sufficiently long after implantation to cause an adverse local response. Bioabsorbable polymers are gradually absorbed or eliminated by the body by hydrolysis, metabolic process, bulk, or surface erosion. Examples of bioabsorbable, biodegradable materials include but are not limited to polycaprolactone (PCL), poly-D, L-lactic acid (DL-PLA), poly-L-lactic acid (L-PLA), poly(lactide-co-glycolide), poly (hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, poly(amino acids), cyanoacrylates, poly(trimethylene carbonate), poly (iminocarbonate), copoly(ether-esters), polyalkylene oxalates, polyphosphazenes, polyiminocarbonates, and aliphatic polycarbonates. Biomolecules such as heparin, fibrin, fibrinogen, cellulose, starch, and collagen are typically also suitable. Examples of biostable polymers include Parylene®, Parylast®, polyurethane (for example, segmented polyurethanes such as Biospan®), polyethylene, polyethlyene terephtalate, ethylene vinyl acetate, silicone and polyethylene oxide.

Therapeutic substances can include, but are not limited to, antineoplastic, antimitotic, antiinflammatory, antiplatelet, anticoagulant, anti fibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include alpha-interferon, genetically engineered epithelial cells, and dexamethasone. In other examples, the therapeutic substance is a radioactive isotope for implantable device usage in radiotherapeutic procedures. Examples of radioactive isotopes include, but are not limited to, phosphorus ($P^{32}$), palladium ($Pd^{103}$), cesium ($Cs^{131}$), Iridium ($I^{192}$) and iodine ($I^{125}$). While the preventative and treatment properties of the foregoing therapeutic substances or agents are well-known to those of ordinary skill in the art, the substances or agents are provided by way of example and are not meant to be limiting. Other therapeutic substances are equally applicable for use with the disclosed methods and compositions.

Figure 8:
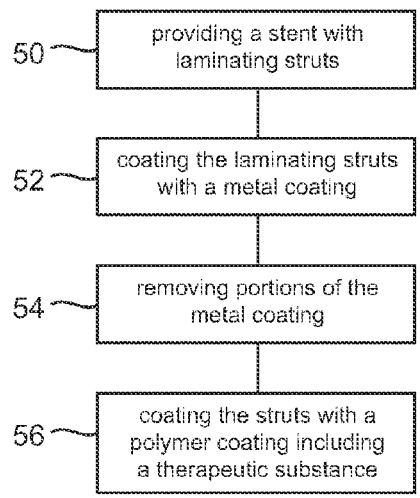
FIG. 8 is a diagram illustrating a method of making the implantable medical device in accordance with an embodiment of the present invention.

FIG. 8 is a diagram showing a method of making a stent in accordance with embodiments of the present invention. Step 50 of the method is to provide a stent with laminated struts. As would be apparent to those skilled in the art, the struts can be any laminated structure, such as a dual layer or tri-layer laminate. Further, the shape or form of the overall stent can be any suitable shape or form. Step 52 of the method is to coat at least a portion of the laminated struts with a metal coating. Step 54 is an optional step of removing portions of the metal coating. Step 56 is an optional step of coating the metal coated laminated struts with a polymeric coating. The polymeric coating may include a therapeutic substance.

Figure 9:
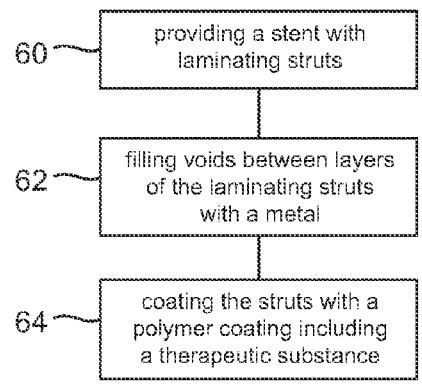
FIG. 9 is a diagram illustrating a method of making the implantable medical device in accordance with an alternative embodiment of the present invention.

FIG. 9 is a diagram showing an alternative method of making a stent in accordance with embodiments of the present invention. Step 60 of the method is to provide a stent with laminated struts. As would be apparent to those skilled in the art, the struts can be any laminated structure, such as a dual layer or tri-layer laminate. Further, the shape or form of the overall stent can be any suitable shape or form. Step 62 of the method is to fill voids between layers of the laminated struts with a metal. Step 62 can be accomplished by sputtering, such as vacuum deposition or ion beam sputtering, chemical vapor deposition (CVD), spraying, dipping, or any other suitable method as would be apparent to one of ordinary skill in the art. Step 64 is an optional step of coating the laminated struts with a polymeric coating. The polymeric coating may include a therapeutic substance.

Figure 10:
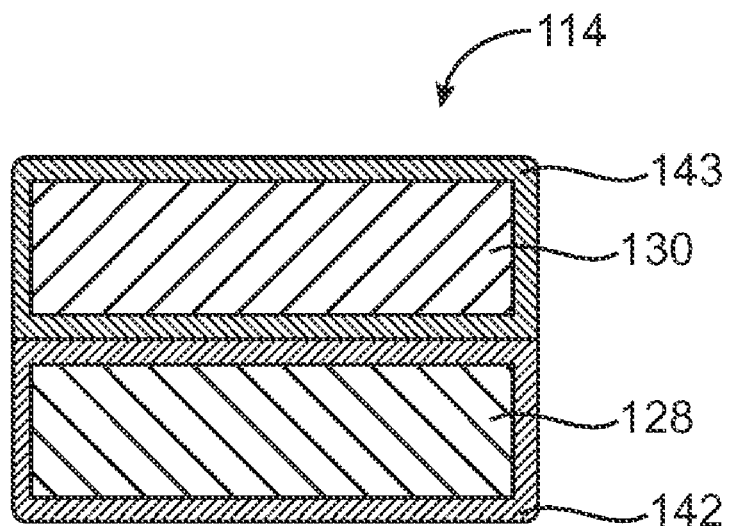
FIG. 10 illustrates a cross-sectional view of an alternative embodiment of a stent strut of the stent of FIG. 1 taken along line A-A.
Figure 11:
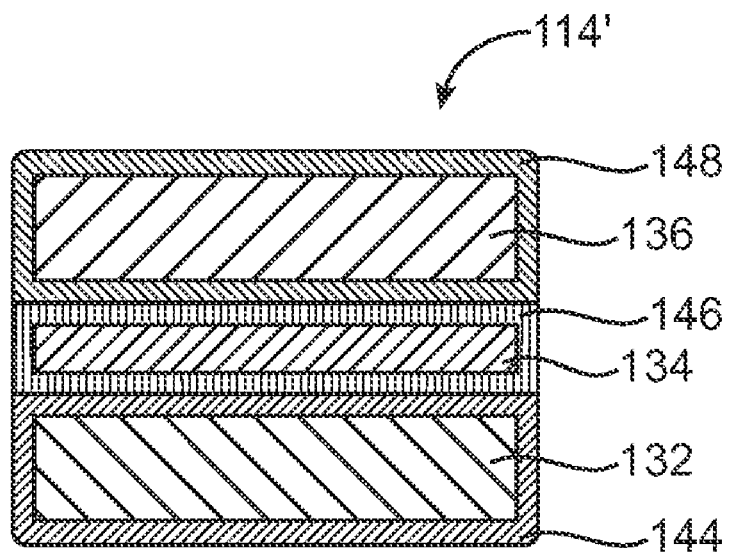
FIG. 11 illustrates a cross-sectional view of an alternative embodiment of a stent strut of the stent of FIG. 1 taken along line A-A.

FIGS. 10 and 11 show alternative embodiments of a strut 114, 114' of a stent. FIG. 10 illustrates strut 114 comprising a first layer 128 and a second layer 130, similar to the embodiment of FIGS. 2 and 4. However, first layer 128 and second layer 130 are coated with a first metal coating 142 and a second metal coating 143, respectively, prior to lamination. Thus, first layer 128 is coated with metal coating 142 and second layer 130 is coated with metal coating 143, and then the coated first layer and the coated second layer are bonded together. Similarly, FIG. 11 illustrates strut 114' comprising a first layer 132, a second layer 134, and third layer 136, similar to the embodiment of FIGS. 3 and 5. However, first layer 132, second layer 134, and third layer 136 are coated with a first metal coating 144, a second metal coating 146, and a third metal coating 148, respectively, prior to lamination. Thus, first layer 132 is coated with first metal coating 144, second layer 134 is coated with second metal coating 146, and third layer 136 is coated with third metal coating 148, then the coated first, second, and third layers are bonded together. The coated layers can be bonded together, for example, by diffusion bonding, friction welding, explosion welding, sintering, hot isostatic pressing (HIP), electroplating, and other bonding techniques as would be apparent to those of ordinary skill in the art. By coating the layers with a metal coating prior to prior to laminating the layers, voids between the layers may be minimized because the metal coatings of each layer will bond together. The metal coatings may be provided by sputtering, such as vacuum deposition or ion beam sputtering, chemical vapor deposition (CVD), spraying, dipping, or other methods known to those skilled in the art.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An Implantable medical device having struts formed into a pattern, the struts comprising:
a laminate core structure; and
a metal coating surrounding said laminate core structure, wherein the metal coating is selected from the group consisting of biocompatible, radiopaque metals,
wherein the laminate core structure comprises:
a first metal layer having an inner surface and an outer surface; and
a second metal layer having an inner surface and an outer surface, wherein the inner surface of said second layer abuts the outer surface of said first layer and does not abut the inner surface of said first layer such that said first layer and said second layer form the laminated core structure; and
longitudinal voids formed between and along the outer edges of said first layer and second layer; and
said metal coating disposed in said longitudinal voids.

2. The implantable medical device of claim 1, wherein said first metal layer and said second metal layer are made from materials selected from the group consisting of stainless steel, nickel titanium alloys, tantalum, platinum-iridium alloys, gold, magnesium, cobalt, nickel, chromium, molybdenum, and combinations or alloys thereof.

3. The implantable medical device of claim 2, wherein the first metal layer and the second metal layer are made from different materials.

4. An implantable medical device having struts formed into a pattern, the struts comprising:
a laminate core structure; and
a metal coating surrounding said laminate core structure, wherein the metal coating is selected from the group consisting of biocompatible, biodegradable metals,
wherein the laminate core structure comprises:
a first metal layer having an inner surface and an outer surface; and
a second metal layer having an inner surface and an outer surface, wherein the inner surface of said second layer abuts the outer surface of said first layer and does not abut the inner surface of said first layer such that said first layer and said second layer form the laminated core structure; and
longitudinal voids formed between and along the outer edges of said first layer and second layer; and
said metal coating disposed in said longitudinal voids.

5. The implantable medical device of claim 4, wherein said first metal layer and said second metal layer are made from materials selected from the group consisting of stainless steel, nickel titanium alloys, tantalum, platinum-iridium alloys, gold, magnesium, cobalt, nickel, chromium, molybdenum, and combinations or alloys thereof.

6. The implantable medical device of claim 4, wherein the first metal layer and the second metal layer are made from different materials.

* * * * *